United States Patent [19]

Buschmann et al.

[11] 4,431,812
[45] Feb. 14, 1984

[54] PYRIDINECARBINOLS

[75] Inventors: Ernst Buschmann; Eberhard Ammermann, both of Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 394,185

[22] Filed: Jul. 1, 1982

[30] Foreign Application Priority Data

Jul. 8, 1981 [DE] Fed. Rep. of Germany ....... 3126819

[51] Int. Cl.³ ............................................ C07D 213/30
[52] U.S. Cl. .................................................... 546/344
[58] Field of Search ......................................... 546/344

[56] References Cited

U.S. PATENT DOCUMENTS

| 2,863,802 | 12/1958 | Pyne | 546/344 |
| 3,396,224 | 8/1968 | Van Heyningen | 546/344 |
| 3,655,359 | 4/1972 | Krumkalns et al. | 71/94 |
| 4,039,675 | 8/1977 | Krumkalns | 424/263 |
| 4,116,665 | 9/1978 | Krumkalns | 71/94 |
| 4,189,486 | 2/1980 | Sauter et al. | 546/344 |

FOREIGN PATENT DOCUMENTS

| 1399 | 4/1979 | European Pat. Off. |
| 498568 | 12/1970 | Switzerland. |
| 1337359 | 11/1973 | United Kingdom. |

OTHER PUBLICATIONS

Chemical Abstracts, Chemical Substance Index, vol. 90 (1979) pp. 5118CS, 5119CS.

Primary Examiner—Norma S. Milestone
Attorney, Agent, or Firm—Keil & Witherspoon

[57] ABSTRACT

Pyridinecarbinols of the formula

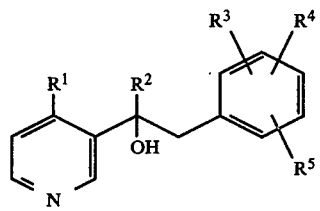

where $R^1$ is hydrogen or alkyl, $R^2$ is alkyl or alkenyl, and $R^3$, $R^4$ and $R^5$ are hydrogen, chlorine, bromine, fluorine or alkyl, plant-physiologically tolerated addition salts of these compounds with acids, and fungicides containing these compounds.

3 Claims, No Drawings

PYRIDINECARBINOLS

The present invention relates to novel pyridine-carbinols and salts of these compounds, to fungicidal agents containing these compounds, and to processes for their preparation.

Fungicidal pyridine derivatives, for example 5-butyl-5-(4-tert.-butylbenzyl)-pyrid-3-yl iminodithiocarbonate, are described in Japanese patent application No. 72/43,334.

We have found that pyridinecarbinols of the formula

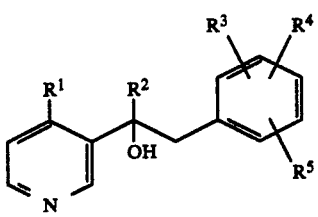

I where $R^1$ is hydrogen or alkyl, $R^2$ is $C_1$-$C_8$-alkyl or alkenyl and $R^3$, $R^4$ and $R^5$ are each, independently of one another, hydrogen, chlorine, bromine, fluorine or alkyl, and the plant-physiologically tolerated addition salts of these compounds with acids have a good fungicidal action, which is superior to that of the known pyridine derivatives.

Examples of $R^1$ are hydrogen and alkyl of 1 to 6 carbon atoms, e.g. methyl, ethyl, propyl, butyl, isobutyl, pentyl and hexyl.

Examples of $R^2$ are $C_1$-$C_6$-alkyl, e.g. methyl, ethyl, propyl, butyl, isobutyl, pentyl, 3,3-dimethyl-butyl and hexyl, or $C_3$-$C_6$-alkenyl, e.g. 3,3-dimethyl-but-1-en-1-yl.

Examples of $R^3$, $R^4$ and $R^5$ are hydrogen, fluorine, chlorine, bromine and $C_1$-$C_4$-alkyl, e.g. methyl, ethyl, propyl, isopropyl, n-butyl, isobutyl and tert.-butyl.

Examples of plant-physiologically tolerated salts of the compounds are the hydrochlorides, hydrobromides, sulfates, phosphates, oxalates, acetates and formates, and adducts with acids derived from surfactants, for example dodecylbenzenesulfonic acid.

The compounds contain one or more asymmetric carbon atoms. They accordingly exist in the form of their optical isomers. The invention embraces both the pure optical isomers and the mixtures of these.

The novel compounds may be prepared by a process wherein an acylpyridine of the formula

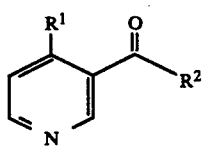

II where $R^1$ and $R^2$ have the above meanings, is reacted, in the presence of a solvent, with an organo-metallic compound of the formula

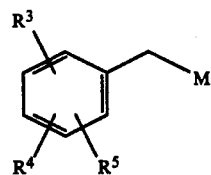

III where M is Li, Na, MgBr or MgCl and $R^3$, $R^4$ and $R^5$ have the above meanings.

Examples of suitable solvents are diethyl ether, tetrahydrofuran, dimethoxyethane and toluene.

Some of the acylpyridines of the formula II are known from R. L. Frank and C. Weatherbee, J.Am.-Chem.Soc. 70 (1948), 3482. The experimental methods described in the said publication for compounds where $R^1$ is H, propyl or butyl and $R^2$ is propyl or butyl may also be readily applied to compounds containing other alkyl radicals.

A further method of synthesis of 3-acylpyridines of the formula II is shown below:

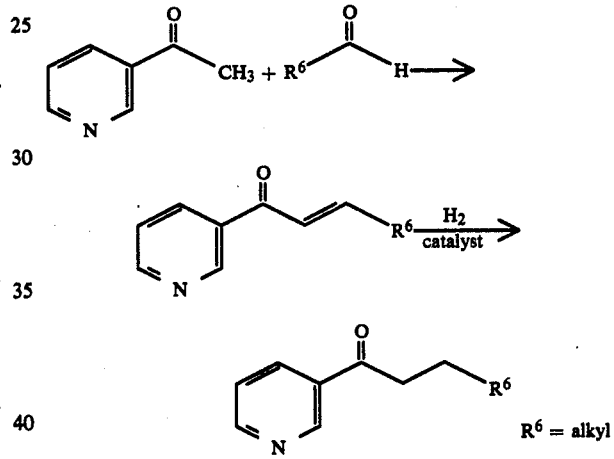

$R^6$ = alkyl

The methods and Example which follow illustrate the preparation of the intermediates and of the novel compounds.

METHOD I

β-tert.-Butylvinyl pyridin-3-yl ketone

A solution of 143 g of pivalaldehyde in 300 ml of ethanol was added dropwise, over four hours, to a solution of 8.3 g of NaOH and 200 g of 3-acetylpyridine in 600 ml of ethanol at room temperature. The mixture was stirred for one hour at room temperature, 18 g of glacial acetic acid were added and the batch was concentrated after 14 hours. The residue was taken up in $CH_2Cl_2/H_2O$. The aqueous phase was extracted with $CH_2Cl_2$. The organic phase was washed with water, dried over $Na_2SO_4$, concentrated and distilled. 95 g of β-tert.-butylvinyl pyridin-3-yl ketone were obtained; boiling point 122°–124° C./0.5 mbar.

METHOD II 3,3-Dimethylbutyl pyridin-3-yl ketone 20 g of a hydrogenation catalyst (5% of Pr and 0.5% of Pd on $Al_2O_3$) were added to a solution of 200 g of β-tert.-butylvinyl pyridin-3-yl ketone in 400 ml of water, the mixture was flushed with $N_2$, and hydrogen was then forced in. The mixture was stirred for 8 hours at 130° C. and 20 bar, the introduction of hydrogen being continued until the pressure remained constant. After the mixture had cooled and the catalyst had been filtered off, the filtrate was concentrated and the residue distilled. 75 g of 3,3-dimethylbutyl pyridin-3-yl ketone were obtained; boiling point 110°–116° C./0.6 mbar.

METHOD III

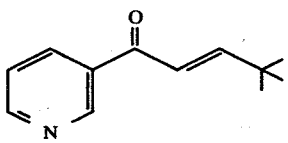

A solution of 143 g of pivalaldehyde in 300 ml of EtOH was added dropwise over 4 hours to a solution of 8.3 g of NaOH and 200 g of 3-acetylpyridine in 600 ml of EtOH at room temperature. The mixture was stirred for a further hour, neutralized with 18 g of glacial acetic acid and concentrated, and the residue was taken up in $CH_2Cl_2/H_2O$. The organic phase was washed repeatedly with water, dried over $Na_2SO_4$ and concentrated. Distillation of the residue gave 95 g of the compound of the above formula, boiling point 122°–124° C./0.4 mbar.

EXAMPLE 1

3,3-Dimethylbutyl-2,4-dichlorobenzyl-pyridin-3-yl-carbinol

A solution of 66.2 g of 2,4-dichlorobenzyl chloride in 150 ml of ether was added dropwise to 8.2 g of Mg in 100 ml of diethyl ether. After 20% of the amount of dichlorobenzyl chloride had been added, the reaction was started by adding a few drops of bromine. After completion of the dropwise addition of the 2,4-dichlorobenzyl chloride solution, the mixture was refluxed for ½ an hour. It was then added dropwise to a solution of 55 g of 3,3-dimethylbutyl pyridin-3-yl ketone in 100 ml of ether. After it had been refluxed for a further two hours, the reaction mixture was hydrolyzed by dropwise addition of saturated aqueous $NH_4Cl$ solution (until the pH was 8), while being cooled with ice. The mixture was stirred for 15 hours at room temperature (20° C.) and extracted with diethyl ether, and the ether phase was washed with water, dried over $Na_2SO_4$, concentrated and distilled. 52 g of 3,3-dimethylbutyl-2,4-dichlorobenzyl-pyridin-3-yl-carbinol (active ingredient No. 36) were obtained; boiling point 196°–202° C./0.5 mbar.

EXAMPLE 2

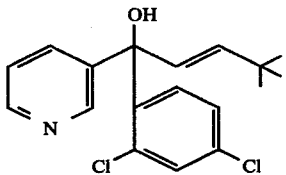

A solution of 38 g of the compound obtained according to III in 100 ml of diethyl ether was added dropwise, at room temperature (20° C.), to a suspension of a Grignard compound, prepared from 49 g of 2,4-dichlorobenzyl chloride and 6 g of Mg, in 200 ml of diethyl ether. The mixture was refluxed for 2 hours, hydrolyzed with ice water and concentrated aqueous $NH_4Cl$ solution, stirred overnight and repeatedly extracted with diethyl ether. The combined organic phases were washed with water, dried over $Na_2SO_4$ and concentrated. Distillation of the residue gave 40 g of compound No. 46, boiling point 198°–208° C./0.5 mbar.

The compounds, in the Table below, whose melting points (m.p.) or boiling points are specified were prepared by similar methods. Their structure was confirmed by elementary analysis. Those compounds for which no physico-chemical data are given can be obtained by the same methods as the compounds actually prepared; it may be expected that because of their similar structure they will have similar effects to those of the compounds investigated in more detail.

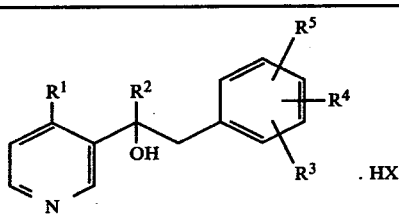

| No. | $R^1$ | $R^2$ | $R^3, R^4, R^5$ | HX | B.p. °C./mbar M.p. |
|---|---|---|---|---|---|
| 1 | H | $CH_3$ | H | HCl | 156 |
| 2 | H | $CH_3$ | 4-Br | — | |
| 3 | H | $CH_3$ | 4-Cl | — | |
| 4 | $CH_3$ | $CH_3$ | 2,4-$Cl_2$ | — | |
| 5 | H | $CH_3$ | 2,4-$Cl_2$ | — | 196–202/0.3 |
| 6 | H | $CH_3$ | 2,4-$Cl_2$ | HCl | 232 |
| 7 | H | $CH_3$ | 3,4-$Cl_2$ | — | 206/0.3 |
| 8 | H | n-$C_3H_7$ | 4-Br | | |
| 9 | H | n-$C_3H_7$ | 2,3,4-$Cl_3$ | — | |
| 10 | H | n-$C_3H_7$ | 4-$CH_3$ | | |
| 11 | H | n-$C_3H_7$ | 2,4-$Cl_2$ | — | 211/0.3 |
| 12 | H | n-$C_3H_7$ | 2,4-$Cl_2$ | HCl | 141 |
| 13 | n-$C_3H_7$ | n-$C_3H_7$ | 2,4-$Cl_2$ | — | 218–222/0.2 |
| 14 | H | n-$C_3H_7$ | 2,4-$Cl_2$ | $HNO_2$ | |
| 15 | H | n-$C_3H_7$ | 4-F | — | |
| 16 | H | iso-$C_3H_7$ | 2,4-$Cl_2$ | — | |
| 17 | H | n-Butyl | 4-Cl | — | 190–196/0.3 |
| 18 | H | n-Butyl | 4-Cl | HCl | 162 |

-continued

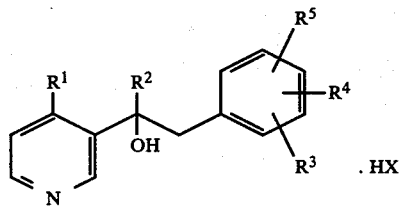

| No. | R¹ | R² | R³, R⁴, R⁵ | HX | B.p. °C./mbar M.p. |
|---|---|---|---|---|---|
| 19 | H | n-Butyl | 2,4-Cl₂ | — | 198–200/0.1 |
| 20 | H | n-Butyl | 2,4-Cl₂ | HCl | 130 |
| 21 | H | n-Butyl | H | — | 160/0.1 |
| 22 | H | n-Butyl | 2,4-Cl₂ | CH₃–(CH₂)₁₁–C₆H₄–SO₃H | resin |
| 23 | H | n-Butyl | 2,4-Cl₂ | Oxalic acid | |
| 24 | n-Butyl | n-Butyl | 2,4-Cl₂ | — | 235–238/0.1 |
| 25 | n-Butyl | n-Butyl | 2,4-Cl₂ | HCl | 159 |
| 26 | n-Butyl | n-Butyl | 4-Cl | HCl | 170 |
| 27 | n-Butyl | n-Butyl | 4-Cl | — | 193–201/0.1 |
| 28 | H | n-Butyl | 4-Br | — | |
| 29 | H | n-Butyl | 4-Br | HCl | |
| 30 | H | n-Pentyl | 2,4-Cl₂ | — | 195–206/0.3 |
| 31 | H | n-Pentyl | 2,4-Cl₂ | HCl | 120 |
| 32 | n-Pentyl | n-Pentyl | 2,4-Cl₂ | — | 223–228/0.2 |
| 33 | n-Pentyl | n-Pentyl | 2,4-Cl₂ | HCl | 149 |
| 34 | H | (CH₂)₂CH(CH₃)₂ | 2,4-Cl₂ | — | 196–202/0.3 |
| 35 | H | (CH₂)₂CH(CH₃)₂ | 2,4-Cl₂ | HCl | 133 |
| 36 | H | (CH₂)₂—t.-Butyl | 2,4-Cl₂ | — | 196–202/0.5 |
| 37 | H | (CH₂)₂—t.-Butyl | 2,4-Cl₂ | HCl | 177 |
| 38 | H | CH₃ | H | — | 142–146/0.2 |
| 39 | H | CH₃ | 4-tert.-Butyl | — | 170–172/0.3 |
| 40 | H | CH₃ | 4-CH₃ | — | 160/0.2 |
| 41 | H | CH₃ | 4-F | — | 150–157/0.2 |
| 42 | H | | n-tert.-Butyl | — | |
| 43 | H | CH₃ | 2,3,4-Cl₃ | | |
| 44 | H | n-Butyl | 2,3,4-Cl₃ | | |
| 45 | H | 3,3-Dimethyl-but-1-en-1-yl | 2,4-Cl₂ | HCl | 128 |
| 46 | H | 3,3-Dimethyl-but-1-en-1-yl | 2,4,-Cl₂ | — | 198–208/0.5 |
| 47 | H | n-Propyl | 2,4-Cl₂ | CH₃—(CH₂)₁₁—C₆H₄—SO₃H | resin |
| 48 | H | n-Butyl | 2,4-Cl₂ | HCl | 180 |
| 49 | H | n-Pentyl | H | — | 168–175/0.3 |

The novel compounds and their salts have an excellent action on a broad spectrum of plant-pathogenic fungi, especially from the Ascomycetes and Basidiomycetes classes. Some of them have a systemic action and may be used as soil and foliar fungicides.

The fungicidal compounds are of particular interest for combating a large number of fungi in various crops or their seed, especially wheat, rye, barley, oats, rice, Indian corn, cotton, soybeans, coffee, sugarcane, fruit, ornamentals in horticulture, vegetables, such as cucumbers, beans and Curcurbitaceae, and grapes for wine.

The novel compounds are particularly suitable for combating the following diseases: *Erysiphe graminis* in cereals, *Erysiphe cichoriacearum* in Cucurbitaceae, *Podosphaera leucotricha* in apples, *Uncinula necator* in grapes, *Erysiphe polygoni* in beans, *Sphaerotheca pannosa* in roses, *Puccinia* species in cereals, *Rhizoctonia solani* in cotton, *Helminthosphorium* species in cereals, *Ustilago* species in cereals and sugarcane, *Rhynchosporium secale* in cereals, and —particularly—*Venturia inaequalis* (apple scab); further, *Botrytis cinerea* in grapes, pimientos and strawberries, *Monilia fructigena* in apples, *Oidium heveae* in rubber plants, *Oidium mangiferae* in mangoes, *Leiveillula taurica* in beans, peas and tomatoes, *Marssonina rosae* in roses, and *Cercospora musae* in bananas.

The compounds are applied by spraying or dusting the plants, or treating the seed with the active ingredients. Application may be effected before or after infection of the plants or seed by the fungi.

The active ingredients of the invention can be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredients. The formulations are prepared in the conventional manner, for example by diluting the active ingredient with solvents and/or carriers, with or without the addition of emulsifiers and dispersants and, where water is used as the diluent, with or without and organic auxiliary solvent. Suitable auxiliaries are, essentially, solvents, for example aromatics, e.g. xylene and benzene, chloroaromatics. e.g. chlorobenzene, paraffins, e.g. petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents generally contain from 0.1 to 95, preferably from 0.5 to 90, wt% of active ingredient.

The application rates depend on the effect desired, and vary from 0.02 to 3 kg of active ingredient per hectare or more.

The fungicides and the ready-to-use formulations prepared therefrom, such as solutions, emulsions, suspensions, powders, dusts, pastes or granules are employed in a conventional manner, for example by spraying, atomizing, dusting, broadcasting, dressing or watering.

Examples of such formulations are given below.

I. 90 parts by weight of compound 5 is mixed with 10 parts by weight of N-methyl-alpha-pyrrolidone. A mixture is obtained which is suitable for application in the form of very fine drops.

II. 20 parts by weight of compound 6 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound 7 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound 11 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 20 parts by weight of compound 12 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound 13 is intimately mixed with 97 parts by weight of particulate kaolin. A dust is obtained containing 3% by weight of the active ingredient.

VII. 30 parts by weight of compound 17 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 18 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound 20 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be mixed and applied with other active ingredients, e.g., herbicides, insecticides, growth regulators, other fungicides and fertilizers. When mixed with other fungicides, the spectrum of fungicidal action is in many cases increased.

The following list of fungicides, with which the compounds according to the invention may be combined, is intended to illustrate and not to restrict the combination possibilites.

Examples of fungicides which may be combined with the active ingredients according to the invention are as follows:
sulfur
dithiocarbamates and derivatives thereof, such as
ferric dimethyldithiocarbamate
zinc dimethyldithiocarbamate
manganese ethylenebisdithiocarbamate
zinc ethylenebisthiocarbamate
tetramethylthiuram disulfide
manganese-zinc ethylenediamine-bisdithiocarbamate
zinc-(,N,N'-propylene-bisdithiocarbamate)
ammonia compley of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
heterocyclic structures, such as
N-(1,1,2,2-tetrachloroethylthio)-tetrahydrophthalimide
N-trichloromethylthiotetrahydrophthalimide
N-trichloromethylthiophthalimide
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone 2-thio-1,3-dithio-(4,5-b)-quinoxaline
methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl-2-thioureido)-benzene and various substances, such as
dodecylguanidine acetate
3-[2-(3,5-dimethyl-2-oxycyclohexyl)-2-hydroxyethyl]-glutarimide hexachlorobenzene
N-dichlorofluoromethylthio-N,N'-dimethyl-N-phenyl-sulfuric acid diamide
D,L-methyl-N-(2,6-dimethylphenyl)-N-(2-furoyl)-alanate
methyl D,L-N-(2,6-dimethylphenyl)-N-(2-methoxyacetyl)-alanate
diisopropyl 5-nitroisophthalate
2,5-dimethylfuran-3-carboxanilide
2,5-dimethylfuran-3-carboxylic acid cyclohexyl amide
2-cyano-N-[(ethylamino)-carbonyl]-2-(methoximino)-acetamide
2-methylbenzoic acid anilide
2-iodobenzoic acid anilide
1-(3,4-dichloroanilino)-formylamino-2,2,2-trichloroethane
2,6-dimethyl-N-tridecylmorpholine and its salts
2,6-dimethyl-N-cyclododecylmorpholine and its salts
1-(1',2',4-triazolyl-1')-1-(4'-chlorophenoxy)-3,3-dimethylbutan-2-one
1-(1',2',4'-triazolyl-1')-1-(4'-chlorophenoxy)-3,3-dimethyl-butan-2-ol
N-(2,6-dimethylphenyl)-N-chloroacetyl-D,L-2-aminobutyrolactone
N-(n-propyl)-N-(2,4,6-trichlorophenoxyethyl)-N'-imidazolylurea
2,4,5-trimethyl-furan-3-carboxanilide
5-methyl-5-vinyl-3-(3,5-dichlorophenyl)-2,4-dioxo-1,3-oxazolidine
5-methoxymethyl-5-methyl-3-(3,5-dichlorophenyl)-2,4-dioxo-1,3-oxazolidine
N-[3-(p-tert.-butylphenyl)-2-methyl-propyl]-cis-2,6-dimethyl-morpholine
1-(2,4-dichlorophenyl)-4,4-dimethyl-2-(1,2,4-triazol-1-yl)-pentan-3-ol
alpha-(2-chlorophenyl)-alpha-(4-fluorophenyl)-5-pyrimidine methanol
alpha-(2-chlorophenyl)-alpha-(4-chlorophenyl)-5-pyrimidine methanol
beta-[(1,1'-biphenyl)-4-yl-oxy]-alpha-(1,1-dimethylethyl)-1H-1,2,4-triazole-1-ethanol
1-[2-(2,4-dichlorophenyl)-4-ethyl-1,3-dioxolan-2-yl-methyl]-1H-1,2,4-triazole
1-[2-(2,4-dichlorophenyl)-4-propyl-1,3-dioxolan-2-yl-methyl]-1H-1,2,4-triazole
1-[N-propyl-N-2-(2,4,6-trichlorophenoxy)-ethyl]-carbamoyl-imidazole
2-cyano-N-(ethylaminocarbonyl)-2-(methoxyimino)-acetamide
N-(1-formylamido-2,2,2-trichloroethyl)-morpholine.

For the following experiments, the prior art compound 5-butyl-5-(4-tert-butylbenzyl)-3-pyridylimino-dithiocarbonate (A) was used for comparison purposes.

EXPERIMENT 1

Action on wheat mildew

Leaves of pot-grown wheat seedlings of the "Jubilar" variety were sprayed with aqueous emulsions, the solids of which consisted of 80% (by weight) of active ingredient and 20% of emulsifier, and dusted, 24 hours after the sprayed-on layer had dried, with spores of wheat mildew (*Erysiphe graminis* var. *tritici*). The plants were then placed in a greenhouse at 20° to 22° C. and 75 to 80% relative humidity. The extent of mildew spread was determined after 7 days.

The results show that for instance active ingredients 5, 6, 11, 12, 17, 18, 19, 20, 26, 30, 31, 34, 35 and 45, applied as 0.025%, 0.006% and 0.0015% spray liquors, have a better fungicidal action (e.g., 97%) than active ingredient A (e.g., 90%).

EXPERIMENT 2

Action on cucumber mildew

The leaves of pot-grown cucumber seedlings of the "Chinesische Schlange" variety were sprayed at the 2-leaf stage with a spore suspension of cucumber mildew (*Erysiphe cichoracearum*). After about 20 hours, the plants were sprayed to runoff with aqueous emulsions consisting (dry basis) of 80% of active ingredient and 20% of emulsifier. After the sprayed-on layer had dried, the plants were set up in the greenhouse at from 20° to 22° C. and a relative humidity of 70 to 80%. To assess the action of the novel compounds, the extent of fungus spread was determined after 14 days.

The results show that for instance active ingredients 5, 6, 7, 11, 12, 13, 17, 18, 19, 20, 24, 25, 26, 30, 31, 32, 33, 34 and 35, applied as 0.025% spray liquors, have a good fungicidal action (e.g., 100%).

EXPERIMENT 3

Action of leaf rust of wheat

Leaves of pot-grown wheat seedlings of the "Jubilar" variety were dusted with spores of rust (*Puccinia recondita*). The pots were then placed in a high humidity (90-95%) chamber at from 20° to 22° C. for 24 hours. During this time, the spores germinated and the germ tubes penetrated into the leaf tissue. The infected plants were then sprayed to run-off with aqueous liquors, the solids comprising 80% of active ingredient. After the spray coating had dried, the test plants were set up in a greenhouse at from 20° to 22° C. and from 65 to 70% relative humidity. After 8 days, the degree of development of the rust fungi on the leaves was determined.

The results show that for instance active ingredients 11, 17, 18, 19, 20, 26, 27, 30, 31 and 35, applied as 0.025% spray liquors, have a better fungicidal action (e.g., 97%) than compounds A (e.g., 60%).

EXPERIMENT 4

Action on Botrytis cinerea in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity to obtain optimum conditions for promoting fungus growth. After 5 days, the disease had spread to such a great extent on the untreated plants that the necroses covered the major portion of the leaves.

The results show that active ingredients 6, 7, 11, 12, 13, 17, 18, 19, 24, 27, 30, 31, 32, 34, 35 and 47, applied as 0.025% spray liquors, have a better fungicidal action (e.g., 97%) than compound A (e.g., 90%).

EXPERIMENT 5

Action on apple scab

The young leaves of pot-grown apple seedlings of the "Golden Delicious" variety were sprayed to runoff with aqueous spray liquors containing (dry basis) 80% of active ingredient and 20% of emulsifier. After the sprayed-on layer had dried, the plants were sprayed with a spore suspension of apple scab (*Venturia inaequalis*). The inoculated plants were then placed for 10 days in a climatic chamber at 20° to 22° C. and a relative humidity of 95%. The extent of fungus spread on the leaves was then determined.

The results show that for instance compounds 5, 7, 11, 12, 13, 19, 20, 24, 30, 34 and 35, applied as 0.0075% spray liquors, have a good fungicidal action (e.g., 97%).

EXPERIMENT 6

Action on grape mildew (*Uncinula necator*)

Potted vines of the "Müller Thurgau" variety, with 5 to 6 well developed leaves, were sprayed to runoff with aqueous spray liquors containing (dry basis) 80% of active ingredient and 20% of emulsifer. After the sprayed-on layer had dried, the plants were inoculated with an aqueous spore suspension of *Uncinula necator* and placed in a greenhouse for 12 days. The extent of fungus spread was then assessed.

The results show that compound 30, applied as a 0.005% spray, has a very good fungicidal action (e.g., 100%).

We claim:

1. A pyridinecarbinol of the formula

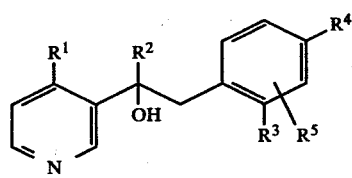

where $R^1$ is hydrogen or alkyl of 1 to 6 carbon atoms, $R^2$ is $C_1$–$C_8$-alkyl and $R^3$ and $R^4$ are chlorine, and $R^5$ is hydrogen, and the plant-physiologically tolerated acid addition salts thereof.

2. A pyridinecarbinol according to claim 1, of the formula

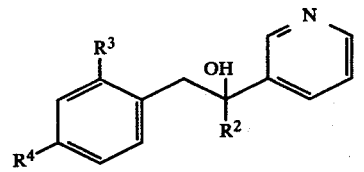

where $R^2$ is $C_1$–$C_8$-alkyl, $R^3$ is chlorine and $R^4$ is chlorine, and the hydrochloride of this compound.

3. A pyridinecarbinol according to claim 1, wherein $R^2$ is n-pentyl.

* * * * *